United States Patent [19]

Robin et al.

[11] Patent Number: 4,972,040

[45] Date of Patent: Nov. 20, 1990

[54] PROCESS FOR THE PREPARATION OF $CHF_2OCHFCF_3$

[75] Inventors: Mark L. Robin, Laffayette, Ind.; Donald F. Halpern, Fanwood, N.J.

[73] Assignee: BOC, Inc., Murray Hill, N.J.

[21] Appl. No.: 391,219

[22] Filed: Jul. 17, 1989

Related U.S. Application Data

[63] Continuation-in-part of Ser. No. 220,716, Jul. 18, 1988, abandoned.

[51] Int. Cl.$^5$ ............................................ C07C 143/68
[52] U.S. Cl. ...................................................... 558/51
[58] Field of Search ............................................ 558/51

[56] References Cited

U.S. PATENT DOCUMENTS 4,879,068 11/1989 Chiarino et al. .................... 570/142

Primary Examiner—Nicky Chan
Attorney, Agent, or Firm—R. Hain Swope; Larry R. Cassett

[57] ABSTRACT

A process for the preparation of a compound having the formula $CF_3CHFOCH_3$ comprising reacting a fluorinating agent with the reaction product of $CF_3CH(OH)OCH_3$ and p-toluene sulfonyl chloride and an improved method for the preparation of $CHF_2OCHFCF_3$ through the use of such compounds.

1 Claim, No Drawings

PROCESS FOR THE PREPARATION OF CHF$_2$OCHFCF$_3$

RELATED APPLICATIONS

This application is a continuation-in-part of U.S. patent application Ser. No. 07/220,716, filed July 18, 1988, now abandoned.

FIELD OF THE INVENTION

The present invention is directed to the field of inhalation anesthetics. In particular, this invention is directed to an improved method for the preparation of CHF$_2$OCHFCF$_3$ utilizing inexpensive starting materials and a novel intermediate.

BACKGROUND OF THE INVENTION

2-Difluoromethoxy-1,1,1,2-tetrafluoroethane (CHF$_2$OCHFCF$_3$) is an important inhalation anesthetic particularly suited for administration to patients during outpatient surgery due to its rapid rate of recovery.

A common method of preparing CHF$_2$OCHFCF$_3$ is by reacting isoflurane (CHF$_2$OCHClCF$_3$) with a fluorinating agent such as BrF$_3$. Isoflurane, however, is expensive and significantly increases the cost of producing CHF$_2$OCHFCF$_3$. Isoflurane's expense is mainly due to its method of preparation from trifluoroethanol (CF$_3$CH$_2$OH) and chlorodifluoromethane (CF$_2$HCl). Trifluoroethanol is both difficult to produce and expensive to obtain.

In view of the above, the compound fluoral methyl hemiacetal (CF$_3$CH(OH)OCH$_3$) is an attractive alternative starting material for the preparation of CHF$_2$OCHFCF$_3$. Fluoral methyl hemiacetal can be economically produced in high yield from the reaction of fluoral (CF$_3$CHO) with methanol, both of which are inexpensive materials.

Fluoral methyl hemiacetal has indeed been used as a starting material for the production of CHF$_2$OCHFCF$_3$. For example, U.S. Pat. No. 3,980,714 discloses reacting the hemiacetal with PCl$_5$ or SOCl$_2$ to thereby replace the hydroxy group with a chlorine atom. In a process disclosed in U.S. Pat. No. 3,981,927, the hemiacetal is reacted with a compound of the formula R'R'NCF$_2$CHFCl to replace the hydroxy group with a fluorine atom. The above procedures are disadvantageous because they employ complex and costly reagents to produce the desired product.

The product of the first reaction, CF$_3$CHClOCH$_3$, is photochemically chlorinated to produce the compound CF$_3$CHClOCHCl$_2$, which is then reacted with a fluorinating agent to produce the desired product CHF$_2$OCHFCF$_3$, as disclosed in German Offen. 2,823,969. The fluorinated product of the second reaction (CF$_3$CHFOCH$_3$) is reacted with chlorine to produce a compound of the formula CF$_3$CHFOCHCl$_2$ which, in turn, is reacted with a fluorinating agent, such as hydrogen fluoride, to produce the desired product CHF$_2$OCHFCF$_3$ This latter reaction is disclosed in U.S. Pat. No. 3,535,388.

These problems are resolved in accordance with the present invention which provides an improved, less costly method for the preparation of CHF$_2$OCHFCF$_3$ from inexpensive starting materials via the hemiacetal.

SUMMARY OF THE INVENTION

The present invention provides a process for the preparation of CHF$_2$OCHFCF$_3$ which comprises reacting fluoral methyl hemiacetal, CF$_3$CH(OH) OCH$_3$, with p-toluene sulfonyl chloride to form the corresponding tosylate compound. The tosylate group is then removed by reaction with a fluorinating agent to form CF$_3$CHFOCH$_3$. The resulting intermediate compound is preferably reacted with chlorine gas to effect chlorine substitution on the terminal carbon. The chlorinated compound is then reacted with a fluorinating agent to obtain high yields of CHF$_2$)CHFCF$_3$.

DETAILED DESCRIPTION OF THE INVENTION

In a first step of the process, fluoral methyl hemiacetal, CF$_3$CH(OH)OCH$_3$, is reacted with p-toluene sulfonyl chloride in the presence of a suitable solvent at ambient temperatures to produce a novel intermediate tosylate compound of the formula

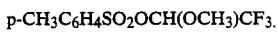

p-CH$_3$C$_6$H$_4$SO$_2$OCH(OCH$_3$)CF$_3$.

The preferred reaction temperature is in the range of from about 11° to 30° C., most preferably from about 20° to 23° C. The preferred solvent is an organic solvent such as dioxane and the reaction is preferably carried out in the presence of an organic base such as, for example, triethylamine. When the reaction is conducted in the presence of triethylamine, the molar ratios of the reactants, i.e. CF$_3$CH(OH)OCH$_3$ to p-toluene sulfonyl chloride to triethylamine, can range from about 1:1:1 to 1:3:3 preferably about 1 to 1.2:1.2.

The tosylate product produced by the above reaction can be separated from the reaction mixture by any convenient procedure, for example, by aqueous work-up of the reaction mass following the removal of precipitated crystals of triethylamine hydrogen chloride. The tosylate compound is then reacted with a fluorinating agent in a suitable solvent to replace the tosylate group with a fluorine atom to thereby produce an intermediate product of the formula CF$_3$CHFOCH$_3$.

The above reaction is typically carried out at a temperature of about 130° to 250° C., preferably in the range of 160°–200° C., in the presence of an organic solvent such as, for example, diethylene glycol or about 100° C. when utilizing water as a solvent. Suitable fluorinating agents include inorganic fluorinating agents, particularly fluorides such as potassium fluoride and cesium fluoride.

1,2,2,2-Tetrafluoroethyl methyl ether (CF$_3$CHFOCH$_3$) prepared as described above can then be used to prepare CF$_3$CHFOCHF$_2$ by any process known in the art, such as that disclosed in German Offen. DE 2,361,058. In such a process, CF$_3$CHFOCHF$_2$ can be conveniently prepared by the photochemical chlorination of CF$_3$CHFOCH$_3$ followed by fluorination with HF in the presence of SbCl$_5$. Alternatively, the compound CF$_3$CHFOCH$_3$ can be reacted with chlorine gas to form CF$_3$CHFOCHCl$_2$ which is, in turn, reacted with a fluorinating agent, as described in U.S. Pat. No. 3,535,388.

Characteristics and descriptions of CF$_3$CHFOCHF$_2$ and anesthetic compositions containing it are disclosed in co-assigned U.S. Pat. No. 4,762,856, incorporated herein by the reference. In accordance with the present invention, the reaction of fluoral methyl hemiacetal with p-toluene sulfonyl chloride strongly favors the formation of the corresponding tosylate compound. As a result, the yield of the desired final product, $CHF_2OCHFCF_3$, is enhanced over previously known methods.

The following examples are provided to more fully illustrate the present invention and are not intended to limit the scope of the invention as encompassed by the claims of the application.

EXAMPLE 1

Preparation of p-$CH_3C_6H_4SO_2OCH(OCH_3)CF_3$ from $CH_3CH(OH)OCH_3$ and p-toluene sulfonyl chloride.

A one liter flask equipped with a thermometer and stir bar is charged with 25.0 grams (0.192) moles) of $CF_3CH(OH)OCH_3$, 32 ml (23 grams, 0.230 moles) of triethylamine and 200 ml of 1,4-dioxane. The flask and contents are then cooled in an ice bath to approximately 12° C., and a solution of 44.0 grams (0.230 moles) of p-toluene sulfonyl chloride in 200 ml of 1,4-dioxane is added dropwise with stirring. The reaction temperature is maintained at approximately 20°–23° C.

Following the addition of the p-toluene sulfonyl chloride, the reaction mixture is stirred at room temperature for two hours. Precipitated triethylamine hydrogen chloride is then removed by filtration and the product isolated by aqueous work-up to yield 41.0 grams (69% yield) of p-$CH_3C_6H_4SO_2OCH(OCH_3)CF_3$ having approximately ninety percent purity. The $^1H$ NMR of the product displays a singlet at 2.5 ppm (aromatic $CH_3$). singlet at 3.6 ppm ($OCH_3$), a quartet (J=4Hz) at 5.6 ppm ($CF_3CH$), and a characteristic pattern for a para-substituted aromatic ring at 7.0–8.0 ppm.

EXAMPLE 2

Preparation of $CF_3CHFOCH_3$ from p-$CH_3C_6H_4SO_2OCH(OCH_3)CF_3$.

A flask is equipped with a thermometer, stir bar and 4-inch Vigreux column to which is attached a reflux head apparatus wherein the cold finger distillation head is maintained at approximately −10° through circulation of a chilled water/methanol mixture. The flask is charged with 20 grams (0.07 mole) of p-$CH_3C_6H_4SO_2OCH(OCH_3)CF_3$, 30 grams (0.20 moles) of cesium flouride, and 100 ml of diethylene glycol. The reaction mass is heated to 180° C. and a total of 2.9 grams of product collected. The $^1H$ NMR shows this material to be 66% $CF_3CHFOCH_3$, at a 33% yield. The $^1H$ NMR of the product containing $CF_3CHFOCH_3$ displays a single at 3.6 ppm ($OCH_3$ and doublet of quarters at 5.2 ppm. The $^{19}F$ NMR displays a singlet at −84 ppm (CHF) and a doublet at −146 ppm.

EXAMPLE 3

Preparation of $CF_3CHFOCH_3$ from p-$CH_3C_6H_4SO_2OCH(OCH_3)CF_3$ in aqueous media.

(a) A solution of 100 g of potassium fluoride dissolved in 100 g of water and 15 g of crude p-$CH_3C_6H_4SO_2OCH(OCH_3)CF_3$ are added to a 500ml single neck flask equipped with a Dean-Stark trap and set for reflux. The reflux condenser is cooled to −10° C. by a circulating water/ethylene glycol solution. The reaction mass is heated to reflux and 1.1 g of distillate are collected. Gas chromatography [SP 1000 on 60/80 mesh Carbopak B (TM Supelco) 20'×⅛" at 190° and He flow of 32 ml/min.] shows the distillate contains 57% of the product, $CF_3CHFOCH_3$.

(b) The procedure of part (a) was repeated utilizing a solution of 60 g cesium fluoride in 60 cc of water, other conditions and quantities being the same. There was obtained 1.2 g of distillate containing 65% $CF_3CHFOCHF_2$(GC analysis).

EXAMPLE 4

Preparation of $CF_3CHFOCHCl_2$ from $CF_3CHFOCH_3$

A total of 305.5 grams (2.34 moles) of $CF_3CHFOCH_3$ was added to a water-jacketed chlorinator fitted with a thermometer, a "Dry-Ice" cold finger-type condenser and a fritted glass gas dispersion tube. The reaction was carried out at 25° C. with gaseous chlorine being bubbled through the solution which was exposed to a source of illumination. The effluent HCl was collected in an aqueous scrubber and aliquots were titrated with standard base. The reaction was continued until slightly less than 2.0 moles of HCl per mole of ether was titrated. The reaction product, $CF_3CHFOCHCl_2$, B.P. 85° C. at 150 mm was recovered by distillation.

EXAMPLE 5

Preparation of $CF_3CHFOCHF_2$ from $CF_3CHFOCHCl_2$

A 1-liter 3-necked stainless steel flask was fitted with a copper "Dry-Ice" cold finger condenser, a stainless steel stirring shaft and gland and a copper gas inlet tube. To the flask there was added 466 grams of $CF_3CHFOCHCl_2$ and 1.5 grams of $SbCl_5$. HF gas was then slowly bubbled through the stirred mixture which was maintained at 0° C. Following the fluorination, a product was recovered and distilled through a 60×2 cm. column packed with glass helices to yield purified material with a boiling point range of 23°–24° C. N.M.R. identified the compound as $CF_3CHFOCHF_2$.

We claim:

1. A compound having the formula p-$CH_3C_6H_4SO_2OCH(OCH_3)CF_3$.

* * * * *

UNITED STATES PATENT AND TRADEMARK OFFICE
CERTIFICATE OF CORRECTION

PATENT NO.  : 4,972,040
DATED       : November 20, 1990
INVENTOR(S) : Mark L. Robin and Donald F. Halpern It is certified that error appears in the above-identified patent and that said Letters Patent is hereby corrected as shown below:

Column 2, line  9, change "$CHF_2)CHFCF_3$" to -- $CHF_2OCHFCF_3$ --;

line 57, change "$CF_3CHFOCH_3$ to -- $CF_3CHClOCH_3$ --;

line 58, change "$CF_3CHFOCHCl_2$" to -- $CF_3CHClOCHCl_2$ --.

Column 3, line 11, change "$CH_3CH(OH)OCH_3$" to -- $CF_3CH(OH)OCH_3$ -- .

Column 4, line 21, change "$CF_3CHFOCHF_2$" to -- $CF_3CHFOCH_3$ -- .

Signed and Sealed this

Sixteenth Day of June, 1992

Attest:

DOUGLAS B. COMER

Attesting Officer　　　Acting Commissioner of Patents and Trademarks